US009291663B2

(12) United States Patent
Grace

(10) Patent No.: US 9,291,663 B2
(45) Date of Patent: Mar. 22, 2016

(54) ALARM FOR LEAD INSULATION ABNORMALITY

(71) Applicant: The Spectranetics Corporation, Colorado Springs, CO (US)

(72) Inventor: Kenneth P. Grace, Woodland Park, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 127 days.

(21) Appl. No.: 13/799,894

(22) Filed: Mar. 13, 2013

(65) Prior Publication Data

US 2014/0277321 A1 Sep. 18, 2014

(51) Int. Cl.
*A61N 1/05* (2006.01)
*G01R 31/12* (2006.01)
*A61N 1/08* (2006.01)

(52) U.S. Cl.
CPC .............. *G01R 31/1263* (2013.01); *A61N 1/05* (2013.01); *A61N 1/08* (2013.01); *A61N 2001/083* (2013.01); *G01R 31/1272* (2013.01)

(58) Field of Classification Search
CPC ..... A61N 2001/083; A61N 1/05; A61N 1/08; G01R 31/1263; G01R 31/1272
See application file for complete search history.

(56) References Cited

U.S. PATENT DOCUMENTS

| 1,663,761 | A | 3/1928 | Johnson |
| 3,400,708 | A | 9/1968 | Scheidt |
| 3,614,953 | A | 10/1971 | Moss |
| 4,051,596 | A | 10/1977 | Hofmann |
| 4,203,444 | A | 5/1980 | Bonnell et al. |
| 4,246,902 | A | 1/1981 | Martinez |
| 4,274,414 | A | 6/1981 | Johnson et al. |
| 4,471,777 | A | 9/1984 | McCorkle, Jr. |
| 4,517,977 | A | 5/1985 | Frost |
| 4,530,368 | A | * 7/1985 | Saulson et al. ................ 607/132 |
| 4,582,056 | A | 4/1986 | McCorkle et al. |
| 4,598,710 | A | 7/1986 | Kleinberg et al. |
| 4,646,738 | A | 3/1987 | Trott |
| 4,662,869 | A | 5/1987 | Wright |
| 4,674,502 | A | 6/1987 | Imonti |
| 4,729,763 | A | 3/1988 | Henrie |
| 4,754,755 | A | 7/1988 | Husted |
| 4,767,403 | A | 8/1988 | Hodge |
| 4,943,289 | A | 7/1990 | Goode et al. |
| 4,950,277 | A | 8/1990 | Farr |
| 4,988,347 | A | 1/1991 | Goode et al. |
| 5,011,482 | A | 4/1991 | Goode et al. |
| 5,013,310 | A | 5/1991 | Goode et al. |
| 5,031,634 | A | 7/1991 | Simon |

(Continued)

FOREIGN PATENT DOCUMENTS

| JP | H05506382 A | 9/1993 |
| JP | 2004516073 A | 6/2004 |

(Continued)

OTHER PUBLICATIONS

U.S. Appl. No. 62/094,808 entitled Multiple Configuration Surgical Cutting Device, filed Dec. 19, 2014.

(Continued)

*Primary Examiner* — Amanda Patton
(74) *Attorney, Agent, or Firm* — Faegre Baker Daniels LLP

(57) ABSTRACT

A system is provided to determine whether an insulating layer of an implanted lead is damaged.

5 Claims, 10 Drawing Sheets

(56) References Cited

U.S. PATENT DOCUMENTS

| | | | |
|---|---|---|---|
| 5,152,744 A | 10/1992 | Krause et al. |
| 5,201,316 A | 4/1993 | Pomeranz et al. |
| 5,207,683 A | 5/1993 | Goode et al. |
| 5,261,877 A | 11/1993 | Fine et al. |
| 5,263,928 A | 11/1993 | Trauthen et al. |
| 5,275,609 A | 1/1994 | Pingleton et al. |
| 5,290,275 A | 3/1994 | Kittrell et al. |
| 5,290,303 A | 3/1994 | Pingleton et al. |
| 5,383,199 A | 1/1995 | Laudenslager et al. |
| 5,395,328 A | 3/1995 | Ockuly et al. |
| 5,423,330 A | 6/1995 | Lee |
| 5,456,680 A | 10/1995 | Taylor et al. |
| 5,484,433 A | 1/1996 | Taylor et al. |
| 5,507,751 A | 4/1996 | Goode et al. |
| 5,562,694 A | 10/1996 | Sauer et al. |
| 5,569,284 A | 10/1996 | Young et al. |
| 5,575,797 A | 11/1996 | Neubauer et al. |
| 5,620,451 A | 4/1997 | Rosborough |
| 5,632,749 A | 5/1997 | Goode et al. |
| 5,651,781 A | 7/1997 | Grace |
| 5,697,936 A | 12/1997 | Shipko et al. |
| 5,718,237 A | 2/1998 | Haaga |
| 5,725,523 A | 3/1998 | Mueller |
| 5,766,164 A | 6/1998 | Mueller et al. |
| 5,782,823 A | 7/1998 | Mueller |
| 5,807,399 A | 9/1998 | Laske et al. |
| 5,814,044 A | 9/1998 | Hooven |
| 5,823,971 A | 10/1998 | Robinson et al. |
| 5,824,026 A | 10/1998 | Diaz |
| 5,863,294 A | 1/1999 | Alden |
| 5,873,886 A | 2/1999 | Larsen et al. |
| 5,879,365 A | 3/1999 | Whitfield et al. |
| 5,893,862 A | 4/1999 | Pratt et al. |
| 5,899,915 A | 5/1999 | Saadat |
| 5,910,150 A | 6/1999 | Saadat |
| 5,916,210 A | 6/1999 | Winston |
| 5,931,848 A | 8/1999 | Saadat |
| 5,941,893 A | 8/1999 | Saadat |
| 5,951,581 A | 9/1999 | Saadat et al. |
| 5,972,012 A | 10/1999 | Ream et al. |
| 5,980,515 A | 11/1999 | Tu |
| 5,980,545 A | 11/1999 | Pacala et al. |
| 6,007,512 A | 12/1999 | Hooven |
| 6,010,476 A | 1/2000 | Saadat |
| 6,019,756 A | 2/2000 | Mueller et al. |
| 6,022,336 A | 2/2000 | Zadno-Azizi et al. |
| 6,027,497 A | 2/2000 | Daniel et al. |
| 6,033,402 A | 3/2000 | Tu et al. |
| 6,036,685 A | 3/2000 | Mueller |
| 6,051,008 A | 4/2000 | Saadat et al. |
| 6,066,131 A | 5/2000 | Mueller et al. |
| 6,080,175 A | 6/2000 | Hogendijk |
| 6,083,237 A | 7/2000 | Huitema et al. |
| 6,099,537 A | 8/2000 | Sugai et al. |
| 6,102,926 A | 8/2000 | Tartaglia et al. |
| 6,117,149 A | 9/2000 | Sorensen et al. |
| 6,120,520 A | 9/2000 | Saadat et al. |
| 6,126,654 A | 10/2000 | Giba et al. |
| 6,136,005 A * | 10/2000 | Goode et al. ............... 606/108 |
| 6,139,543 A | 10/2000 | Esch et al. |
| 6,152,909 A | 11/2000 | Bagaoisan et al. |
| 6,152,918 A | 11/2000 | Padilla et al. |
| 6,156,049 A | 12/2000 | Lovato et al. |
| 6,159,203 A | 12/2000 | Sinofsky |
| 6,159,225 A | 12/2000 | Makower |
| 6,162,214 A | 12/2000 | Mueller et al. |
| 6,165,188 A | 12/2000 | Saadat et al. |
| 6,167,315 A | 12/2000 | Coe et al. |
| 6,174,307 B1 | 1/2001 | Daniel et al. |
| 6,190,352 B1 | 2/2001 | Haarala et al. |
| 6,190,353 B1 | 2/2001 | Makower et al. |
| 6,203,537 B1 | 3/2001 | Adrian |
| 6,210,400 B1 | 4/2001 | Hebert et al. |
| 6,228,076 B1 | 5/2001 | Winston et al. |
| 6,235,044 B1 | 5/2001 | Root et al. |
| 6,241,692 B1 | 6/2001 | Tu et al. |
| 6,245,011 B1 | 6/2001 | Dudda et al. |
| 6,251,121 B1 | 6/2001 | Saadat |
| 6,258,083 B1 | 7/2001 | Daniel et al. |
| 6,290,668 B1 | 9/2001 | Gregory et al. |
| 6,315,774 B1 | 11/2001 | Daniel et al. |
| 6,324,434 B2 | 11/2001 | Coe et al. |
| 6,379,351 B1 | 4/2002 | Thapliyal et al. |
| 6,395,002 B1 | 5/2002 | Ellman et al. |
| 6,398,773 B1 | 6/2002 | Bagaoisan et al. |
| 6,402,771 B1 | 6/2002 | Palmer et al. |
| 6,402,781 B1 | 6/2002 | Langberg et al. |
| 6,419,674 B1 | 7/2002 | Bowser et al. |
| 6,419,684 B1 | 7/2002 | Heisler et al. |
| 6,423,051 B1 | 7/2002 | Kaplan et al. |
| 6,428,539 B1 | 8/2002 | Baxter et al. |
| 6,428,556 B1 | 8/2002 | Chin |
| 6,432,119 B1 | 8/2002 | Saadat |
| 6,436,054 B1 | 8/2002 | Viola et al. |
| 6,436,114 B1 | 8/2002 | Novak et al. |
| 6,454,741 B1 | 9/2002 | Muni et al. |
| 6,454,758 B1 | 9/2002 | Thompson et al. |
| 6,461,349 B1 | 10/2002 | Elbrecht et al. |
| 6,478,777 B1 | 11/2002 | Honeck et al. |
| 6,488,636 B2 | 12/2002 | Bryan et al. |
| 6,500,182 B2 | 12/2002 | Foster |
| 6,512,959 B1 | 1/2003 | Gomperz et al. |
| 6,527,752 B1 | 3/2003 | Bosley et al. |
| 6,537,314 B2 | 3/2003 | Langberg et al. |
| 6,540,865 B1 | 4/2003 | Miekka et al. |
| 6,554,779 B2 | 4/2003 | Viola et al. |
| 6,558,382 B2 | 5/2003 | Jahns et al. |
| 6,565,588 B1 | 5/2003 | Clement et al. |
| 6,569,082 B1 | 5/2003 | Chin |
| 6,575,997 B1 | 6/2003 | Palmer et al. |
| 6,592,607 B1 | 7/2003 | Palmer et al. |
| 6,595,982 B2 | 7/2003 | Sekino et al. |
| 6,599,296 B1 | 7/2003 | Gillick et al. |
| 6,602,241 B2 | 8/2003 | Makower et al. |
| 6,607,547 B1 | 8/2003 | Chin |
| 6,610,046 B1 | 8/2003 | Usami et al. |
| 6,613,013 B2 | 9/2003 | Haarala et al. |
| 6,620,153 B2 | 9/2003 | Mueller et al. |
| 6,620,160 B2 | 9/2003 | Lewis et al. |
| 6,620,180 B1 | 9/2003 | Bays et al. |
| 6,641,590 B1 | 11/2003 | Palmer et al. |
| 6,652,480 B1 | 11/2003 | Imran et al. |
| 6,652,548 B2 | 11/2003 | Evans et al. |
| 6,660,021 B1 | 12/2003 | Palmer et al. |
| 6,663,626 B2 | 12/2003 | Truckai et al. |
| 6,669,685 B1 | 12/2003 | Rizoiu et al. |
| 6,673,090 B2 | 1/2004 | Root et al. |
| 6,687,548 B2 | 2/2004 | Goode |
| 6,702,813 B1 | 3/2004 | Baxter et al. |
| 6,706,018 B2 | 3/2004 | Westlund et al. |
| 6,706,052 B1 | 3/2004 | Chin |
| 6,706,065 B2 | 3/2004 | Langberg et al. |
| 6,709,456 B2 | 3/2004 | Langberg et al. |
| 6,712,773 B1 | 3/2004 | Viola |
| 6,712,826 B2 | 3/2004 | Lui |
| 6,772,014 B2 | 8/2004 | Coe et al. |
| 6,802,838 B2 | 10/2004 | Loeb et al. |
| 6,805,692 B2 | 10/2004 | Muni et al. |
| 6,810,882 B2 | 11/2004 | Langberg et al. |
| 6,818,001 B2 | 11/2004 | Wulfman et al. |
| 6,860,860 B2 | 3/2005 | Viola |
| 6,871,085 B2 | 3/2005 | Sommer |
| 6,884,240 B1 | 4/2005 | Dykes |
| 6,887,238 B2 | 5/2005 | Jahns et al. |
| 6,893,450 B2 | 5/2005 | Foster |
| 6,913,612 B2 | 7/2005 | Palmer et al. |
| 6,962,585 B2 | 11/2005 | Poleo et al. |
| 6,979,290 B2 | 12/2005 | Mourlas et al. |
| 6,979,319 B2 | 12/2005 | Manning et al. |
| 6,989,028 B2 | 1/2006 | Lashinski et al. |
| 6,999,809 B2 | 2/2006 | Currier et al. |
| 7,004,956 B2 | 2/2006 | Palmer et al. |
| 7,011,682 B2 | 3/2006 | Lashinski et al. |
| 7,022,133 B2 | 4/2006 | Yee et al. |

(56) References Cited

U.S. PATENT DOCUMENTS

| | | |
|---|---|---|
| 7,033,335 B2 | 4/2006 | Haarala et al. |
| 7,033,344 B2 | 4/2006 | Imran |
| 7,033,357 B2 | 4/2006 | Baxter et al. |
| 7,060,061 B2 | 6/2006 | Altshuler et al. |
| 7,063,693 B2 | 6/2006 | Guenst |
| 7,077,856 B2 | 7/2006 | Whitman |
| 7,092,765 B2 | 8/2006 | Geske et al. |
| 7,104,983 B2 | 9/2006 | Grasso et al. |
| 7,114,642 B2 | 10/2006 | Whitman |
| 7,117,039 B2 | 10/2006 | Manning et al. |
| 7,149,587 B2 | 12/2006 | Wardle et al. |
| 7,151,965 B2 | 12/2006 | Osypka |
| 7,189,207 B2 | 3/2007 | Viola |
| 7,191,015 B2 | 3/2007 | Lamson et al. |
| 7,192,430 B2 | 3/2007 | Truckai et al. |
| 7,204,824 B2 | 4/2007 | Moulis |
| 7,214,180 B2 | 5/2007 | Chin |
| 7,226,459 B2 | 6/2007 | Cesarini et al. |
| 7,238,179 B2 | 7/2007 | Brucker et al. |
| 7,238,180 B2 | 7/2007 | Mester et al. |
| 7,252,641 B2 | 8/2007 | Thompson et al. |
| 7,264,587 B2 | 9/2007 | Chin |
| 7,273,478 B2 | 9/2007 | Appling et al. |
| 7,276,052 B2 | 10/2007 | Kobayashi et al. |
| 7,288,096 B2 | 10/2007 | Chin |
| 7,296,577 B2 | 11/2007 | Lashinski et al. |
| 7,306,588 B2 | 12/2007 | Loeb et al. |
| 7,326,226 B2 | 2/2008 | Root et al. |
| 7,328,071 B1 | 2/2008 | Stehr et al. |
| 7,344,546 B2 | 3/2008 | Wulfman et al. |
| 7,357,794 B2 | 4/2008 | Makower et al. |
| 7,359,756 B2 | 4/2008 | Goode |
| 7,369,901 B1 | 5/2008 | Morgan et al. |
| 7,396,354 B2 | 7/2008 | Rychnovsky et al. |
| 7,398,781 B1 | 7/2008 | Chin |
| 7,449,010 B1 | 11/2008 | Hayase et al. |
| 7,462,167 B2 | 12/2008 | Kratz et al. |
| 7,485,127 B2 | 2/2009 | Nistal |
| 7,494,484 B2 | 2/2009 | Beck et al. |
| 7,507,252 B2 | 3/2009 | Lashinski et al. |
| 7,509,169 B2 | 3/2009 | Eigler et al. |
| 7,510,576 B2 | 3/2009 | Langberg et al. |
| 7,513,877 B2 | 4/2009 | Viola |
| 7,513,892 B1 | 4/2009 | Haarala et al. |
| 7,526,342 B2 | 4/2009 | Chin et al. |
| 7,537,602 B2 | 5/2009 | Whitman |
| 7,540,865 B2 | 6/2009 | Griffin et al. |
| 7,544,197 B2 | 6/2009 | Kelsch et al. |
| 7,559,941 B2 | 7/2009 | Zannis et al. |
| D600,792 S | 9/2009 | Eubanks et al. |
| 7,591,790 B2 | 9/2009 | Pflueger |
| 7,597,698 B2 | 10/2009 | Chin |
| 7,606,615 B2 | 10/2009 | Makower et al. |
| 7,611,474 B2 | 11/2009 | Hibner et al. |
| 7,637,904 B2 | 12/2009 | Wingler et al. |
| 7,645,286 B2 | 1/2010 | Catanese et al. |
| 7,648,466 B2 | 1/2010 | Stephens et al. |
| 7,651,503 B1 | 1/2010 | Coe et al. |
| 7,651,504 B2 | 1/2010 | Goode et al. |
| D610,259 S | 2/2010 | Way et al. |
| D611,146 S | 3/2010 | Way et al. |
| 7,674,272 B2 | 3/2010 | Torrance et al. |
| 7,695,485 B2 | 4/2010 | Whitman et al. |
| 7,695,512 B2 | 4/2010 | Lashinski et al. |
| 7,697,996 B2 | 4/2010 | Manning et al. |
| 7,713,231 B2 | 5/2010 | Wulfman et al. |
| 7,713,235 B2 | 5/2010 | Torrance et al. |
| 7,713,281 B2 | 5/2010 | Leeflang et al. |
| 7,722,549 B2 | 5/2010 | Nakao |
| 7,740,626 B2 | 6/2010 | Takayama et al. |
| 7,743,960 B2 | 6/2010 | Whitman et al. |
| D619,252 S | 7/2010 | Way et al. |
| D619,253 S | 7/2010 | Way et al. |
| 7,758,594 B2 | 7/2010 | Lamson et al. |
| 7,758,613 B2 | 7/2010 | Whitman |
| D621,939 S | 8/2010 | Way et al. |
| 7,766,923 B2 | 8/2010 | Catanese et al. |
| 7,780,682 B2 | 8/2010 | Catanese et al. |
| 7,780,694 B2 | 8/2010 | Palmer et al. |
| 7,794,411 B2 | 9/2010 | Ritchart et al. |
| 7,798,813 B1 | 9/2010 | Harrel |
| 7,803,151 B2 | 9/2010 | Whitman |
| 7,806,835 B2 | 10/2010 | Hibner et al. |
| 7,811,281 B1 | 10/2010 | Rentrop |
| 7,815,655 B2 | 10/2010 | Catanese et al. |
| 7,842,009 B2 | 11/2010 | Torrance et al. |
| 7,845,538 B2 | 12/2010 | Whitman |
| 7,858,038 B2 | 12/2010 | Andreyko et al. |
| 7,875,018 B2 | 1/2011 | Tockman et al. |
| 7,875,049 B2 | 1/2011 | Eversull et al. |
| 7,890,186 B2 | 2/2011 | Wardle et al. |
| 7,890,192 B1 | 2/2011 | Kelsch et al. |
| 7,896,879 B2 | 3/2011 | Solsberg et al. |
| 7,896,891 B2 | 3/2011 | Catanese et al. |
| 7,905,889 B2 | 3/2011 | Catanese et al. |
| 7,909,836 B2 | 3/2011 | McLean et al. |
| 7,914,464 B2 | 3/2011 | Burdorff et al. |
| 7,914,542 B2 | 3/2011 | Lamson et al. |
| D635,671 S | 4/2011 | Way et al. |
| 7,918,230 B2 | 4/2011 | Whitman et al. |
| 7,918,803 B2 | 4/2011 | Ritchart et al. |
| 7,930,040 B1 | 4/2011 | Kelsch et al. |
| 7,935,146 B2 | 5/2011 | Langberg et al. |
| 7,938,786 B2 | 5/2011 | Ritchie et al. |
| 7,942,830 B2 | 5/2011 | Solsberg et al. |
| 7,951,071 B2 | 5/2011 | Whitman et al. |
| 7,951,158 B2 | 5/2011 | Catanese et al. |
| 7,963,040 B2 | 6/2011 | Shan et al. |
| 7,963,433 B2 | 6/2011 | Whitman et al. |
| 7,974,710 B2 | 7/2011 | Seifert |
| 7,981,049 B2 | 7/2011 | Ritchie et al. |
| 7,981,050 B2 | 7/2011 | Ritchart et al. |
| 7,981,128 B2 | 7/2011 | To et al. |
| 7,988,726 B2 | 8/2011 | Langberg et al. |
| 7,991,258 B2 | 8/2011 | Temelkuran et al. |
| 7,992,758 B2 | 8/2011 | Whitman et al. |
| 7,993,350 B2 | 8/2011 | Ventura et al. |
| 7,993,351 B2 | 8/2011 | Worley et al. |
| 7,993,359 B1 | 8/2011 | Atwell et al. |
| 8,007,469 B2 | 8/2011 | Duffy |
| 8,007,488 B2 | 8/2011 | Ravenscroft |
| 8,007,503 B2 | 8/2011 | Catanese et al. |
| 8,007,506 B2 | 8/2011 | To et al. |
| 8,016,748 B2 | 9/2011 | Mourlas et al. |
| 8,016,844 B2 | 9/2011 | Privitera et al. |
| 8,016,855 B2 | 9/2011 | Whitman et al. |
| 8,016,858 B2 | 9/2011 | Whitman |
| 8,021,373 B2 | 9/2011 | Whitman et al. |
| 8,025,199 B2 | 9/2011 | Whitman et al. |
| 8,043,309 B2 | 10/2011 | Catanese et al. |
| RE42,959 E | 11/2011 | Saadat et al. |
| 8,052,616 B2 | 11/2011 | Andrisek et al. |
| 8,052,659 B2 | 11/2011 | Ravenscroft et al. |
| 8,056,786 B2 | 11/2011 | Whitman et al. |
| 8,056,791 B2 | 11/2011 | Whitman |
| 8,070,762 B2 | 12/2011 | Escudero et al. |
| 8,090,430 B2 | 1/2012 | Makower et al. |
| 8,097,012 B2 | 1/2012 | Kagarise |
| 8,100,920 B2 | 1/2012 | Gambale et al. |
| 8,118,208 B2 | 2/2012 | Whitman |
| 8,126,570 B2 | 2/2012 | Manning et al. |
| 8,128,577 B2 | 3/2012 | Viola |
| 8,128,636 B2 | 3/2012 | Lui et al. |
| 8,133,214 B2 | 3/2012 | Hayase et al. |
| 8,137,377 B2 | 3/2012 | Palmer et al. |
| 8,142,442 B2 | 3/2012 | Palmer et al. |
| 8,142,446 B2 | 3/2012 | Shan |
| RE43,300 E | 4/2012 | Saadat et al. |
| 8,157,815 B2 | 4/2012 | Catanese et al. |
| 8,186,559 B1 | 5/2012 | Whitman |
| 8,187,204 B2 | 5/2012 | Miller et al. |
| 8,192,430 B2 | 6/2012 | Goode et al. |
| 8,202,229 B2 | 6/2012 | Miller et al. |
| 8,206,409 B2 | 6/2012 | Privitera et al. |

(56) References Cited

U.S. PATENT DOCUMENTS

| | | |
|---|---|---|
| 8,211,118 B2 | 7/2012 | Catanese et al. |
| 8,216,254 B2 | 7/2012 | McLean et al. |
| 8,235,916 B2 | 8/2012 | Whiting et al. |
| 8,236,016 B2 | 8/2012 | To et al. |
| 8,239,039 B2 | 8/2012 | Zarembo et al. |
| 8,241,272 B2 | 8/2012 | Arnold et al. |
| 8,251,916 B2 | 8/2012 | Speeg et al. |
| 8,252,015 B2 | 8/2012 | Leeflang et al. |
| 8,257,312 B2 | 9/2012 | Duffy |
| 8,272,554 B2 | 9/2012 | Whitman et al. |
| 8,273,078 B2 | 9/2012 | Muenker |
| 8,295,947 B2 | 10/2012 | Lamson et al. |
| 8,303,511 B2 | 11/2012 | Eigler et al. |
| 8,323,240 B2 | 12/2012 | Wulfman et al. |
| 8,326,437 B2 | 12/2012 | Cully et al. |
| 8,333,740 B2 | 12/2012 | Shippert |
| 8,333,776 B2 | 12/2012 | Cheng et al. |
| 8,337,516 B2 | 12/2012 | Escudero et al. |
| 8,343,167 B2 | 1/2013 | Henson |
| 8,343,187 B2 | 1/2013 | Lamson et al. |
| 8,353,899 B1 | 1/2013 | Wells et al. |
| 8,361,094 B2 | 1/2013 | To et al. |
| 8,364,280 B2 | 1/2013 | Marnfeldt et al. |
| 8,372,098 B2 | 2/2013 | Tran |
| 8,394,110 B2 | 3/2013 | Catanese et al. |
| 8,394,113 B2 | 3/2013 | Wei et al. |
| 8,425,535 B2 | 4/2013 | McLean et al. |
| 8,942,798 B2 * | 1/2015 | Armstrong et al. ............... 607/2 |
| 8,961,551 B2 | 2/2015 | Taylor |
| 2001/0005789 A1 | 6/2001 | Root et al. |
| 2001/0016717 A1 | 8/2001 | Haarala et al. |
| 2001/0025174 A1 | 9/2001 | Daniel et al. |
| 2001/0031981 A1 | 10/2001 | Evans et al. |
| 2001/0039427 A1 | 11/2001 | Dinger et al. |
| 2001/0041899 A1 | 11/2001 | Foster |
| 2001/0044568 A1 | 11/2001 | Langberg et al. |
| 2002/0002372 A1 | 1/2002 | Jahns et al. |
| 2002/0007204 A1 | 1/2002 | Goode |
| 2002/0010475 A1 | 1/2002 | Lui |
| 2002/0010487 A1 | 1/2002 | Evans et al. |
| 2002/0016628 A1 | 2/2002 | Langberg et al. |
| 2002/0045811 A1 | 4/2002 | Kittrell et al. |
| 2002/0065543 A1 | 5/2002 | Gomperz et al. |
| 2002/0068954 A1 | 6/2002 | Foster |
| 2002/0087151 A1 | 7/2002 | Mody et al. |
| 2002/0103477 A1 | 8/2002 | Grasso et al. |
| 2002/0103532 A1 | 8/2002 | Langberg et al. |
| 2002/0103533 A1 | 8/2002 | Langberg et al. |
| 2002/0123785 A1 | 9/2002 | Zhang et al. |
| 2002/0151961 A1 | 10/2002 | Lashinski et al. |
| 2002/0183735 A1 | 12/2002 | Edwards et al. |
| 2002/0188278 A1 | 12/2002 | Tockman et al. |
| 2003/0009146 A1 | 1/2003 | Muni et al. |
| 2003/0036788 A1 | 2/2003 | Coe et al. |
| 2003/0050630 A1 | 3/2003 | Mody et al. |
| 2003/0050631 A1 | 3/2003 | Mody et al. |
| 2003/0055444 A1 | 3/2003 | Evans et al. |
| 2003/0055445 A1 | 3/2003 | Evans et al. |
| 2003/0069575 A1 | 4/2003 | Chin et al. |
| 2003/0073985 A1 | 4/2003 | Mueller et al. |
| 2003/0078562 A1 | 4/2003 | Makower et al. |
| 2003/0105451 A1 | 6/2003 | Westlund et al. |
| 2003/0125619 A1 | 7/2003 | Manning et al. |
| 2003/0167056 A1 | 9/2003 | Jahns et al. |
| 2003/0187460 A1 | 10/2003 | Chin et al. |
| 2003/0187461 A1 | 10/2003 | Chin |
| 2003/0199916 A1 | 10/2003 | Yee et al. |
| 2003/0199921 A1 | 10/2003 | Palmer et al. |
| 2003/0204202 A1 | 10/2003 | Palmer et al. |
| 2003/0208209 A1 | 11/2003 | Gambale et al. |
| 2003/0229323 A1 | 12/2003 | Haarala et al. |
| 2003/0229353 A1 | 12/2003 | Cragg |
| 2004/0006358 A1 | 1/2004 | Wulfman et al. |
| 2004/0010248 A1 | 1/2004 | Appling et al. |
| 2004/0015193 A1 | 1/2004 | Lamson et al. |
| 2004/0019359 A1 | 1/2004 | Worley et al. |
| 2004/0049208 A1 | 3/2004 | Hill et al. |
| 2004/0054368 A1 | 3/2004 | Truckai et al. |
| 2004/0054388 A1 | 3/2004 | Osypka |
| 2004/0059348 A1 | 3/2004 | Geske et al. |
| 2004/0064024 A1 | 4/2004 | Sommer |
| 2004/0068256 A1 | 4/2004 | Rizoiu et al. |
| 2004/0068288 A1 | 4/2004 | Palmer et al. |
| 2004/0093016 A1 | 5/2004 | Root et al. |
| 2004/0102804 A1 | 5/2004 | Chin |
| 2004/0102841 A1 | 5/2004 | Langberg et al. |
| 2004/0111101 A1 | 6/2004 | Chin |
| 2004/0116939 A1 | 6/2004 | Goode |
| 2004/0133220 A1 | 7/2004 | Lashinski et al. |
| 2004/0138562 A1 | 7/2004 | Makower et al. |
| 2004/0138744 A1 | 7/2004 | Lashinski et al. |
| 2004/0143284 A1 | 7/2004 | Chin |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0153096 A1 | 8/2004 | Goode et al. |
| 2004/0153098 A1 | 8/2004 | Chin et al. |
| 2004/0172116 A1 | 9/2004 | Seifert et al. |
| 2004/0176840 A1 | 9/2004 | Langberg et al. |
| 2004/0181249 A1 | 9/2004 | Torrance et al. |
| 2004/0216748 A1 | 11/2004 | Chin |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0235611 A1 | 11/2004 | Nistal |
| 2004/0236312 A1 | 11/2004 | Nistal et al. |
| 2004/0236397 A1 | 11/2004 | Coe et al. |
| 2004/0243123 A1 | 12/2004 | Grasso et al. |
| 2004/0243162 A1 | 12/2004 | Wulfman et al. |
| 2004/0254534 A1 | 12/2004 | Bjorkman et al. |
| 2004/0260322 A1 | 12/2004 | Rudko et al. |
| 2004/0267276 A1 | 12/2004 | Camino et al. |
| 2004/0267304 A1 | 12/2004 | Zannis et al. |
| 2005/0004644 A1 | 1/2005 | Kelsch et al. |
| 2005/0025798 A1 | 2/2005 | Moulis |
| 2005/0027337 A1 | 2/2005 | Rudko et al. |
| 2005/0038419 A9 | 2/2005 | Arnold et al. |
| 2005/0054948 A1 | 3/2005 | Goldenberg |
| 2005/0060030 A1 | 3/2005 | Lashinski et al. |
| 2005/0065561 A1 | 3/2005 | Manning et al. |
| 2005/0090748 A1 | 4/2005 | Makower et al. |
| 2005/0096740 A1 | 5/2005 | Langberg et al. |
| 2005/0131399 A1 | 6/2005 | Loeb et al. |
| 2005/0149104 A1 | 7/2005 | Leeflang et al. |
| 2005/0149105 A1 | 7/2005 | Leeflang et al. |
| 2005/0197623 A1 | 9/2005 | Leeflang et al. |
| 2005/0222607 A1 | 10/2005 | Palmer et al. |
| 2005/0228402 A1 | 10/2005 | Hofmann |
| 2005/0228452 A1 | 10/2005 | Mourlas et al. |
| 2005/0251116 A1 | 11/2005 | Steinke et al. |
| 2005/0259942 A1 | 11/2005 | Temelkuran et al. |
| 2005/0267557 A1 | 12/2005 | Flynn et al. |
| 2005/0273090 A1 | 12/2005 | Nieman et al. |
| 2005/0283143 A1 | 12/2005 | Rizoiu |
| 2005/0288596 A1 | 12/2005 | Eigler et al. |
| 2005/0288604 A1 | 12/2005 | Eigler et al. |
| 2005/0288654 A1 | 12/2005 | Nieman et al. |
| 2006/0041250 A1 | 2/2006 | Poleo |
| 2006/0052660 A1 | 3/2006 | Chin |
| 2006/0084839 A1 | 4/2006 | Mourlas et al. |
| 2006/0100663 A1 | 5/2006 | Palmer et al. |
| 2006/0116746 A1 | 6/2006 | Chin |
| 2006/0116757 A1 | 6/2006 | Lashinski et al. |
| 2006/0167417 A1 | 7/2006 | Kratz et al. |
| 2006/0173440 A1 | 8/2006 | Lamson et al. |
| 2006/0217755 A1 | 9/2006 | Eversull et al. |
| 2006/0229490 A1 | 10/2006 | Chin |
| 2006/0235431 A1 | 10/2006 | Goode et al. |
| 2006/0247751 A1 | 11/2006 | Seifert |
| 2006/0253179 A1 | 11/2006 | Goode et al. |
| 2006/0265042 A1 | 11/2006 | Catanese et al. |
| 2006/0276871 A1 | 12/2006 | Lamson et al. |
| 2006/0287574 A1 | 12/2006 | Chin |
| 2007/0015964 A1 | 1/2007 | Eversull et al. |

(56) References Cited

U.S. PATENT DOCUMENTS

| | | |
|---|---|---|
| 2007/0016130 A1 | 1/2007 | Leeflang et al. |
| 2007/0021812 A1 | 1/2007 | Manning et al. |
| 2007/0049929 A1 | 3/2007 | Catanese et al. |
| 2007/0050003 A1 | 3/2007 | Zarembo et al. |
| 2007/0083217 A1 | 4/2007 | Eversull et al. |
| 2007/0100410 A1 | 5/2007 | Lamson et al. |
| 2007/0106328 A1 | 5/2007 | Wardle et al. |
| 2007/0129710 A1 | 6/2007 | Rudko et al. |
| 2007/0142846 A1 | 6/2007 | Catanese et al. |
| 2007/0197861 A1 | 8/2007 | Reiley et al. |
| 2007/0198020 A1 | 8/2007 | Reiley et al. |
| 2007/0232981 A1 | 10/2007 | Ravenscroft et al. |
| 2007/0276412 A1 | 11/2007 | Catanese et al. |
| 2007/0293853 A1 | 12/2007 | Truckai et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0015625 A1 | 1/2008 | Ventura et al. |
| 2008/0021484 A1 | 1/2008 | Catanese et al. |
| 2008/0021485 A1 | 1/2008 | Catanese et al. |
| 2008/0033232 A1 | 2/2008 | Catanese et al. |
| 2008/0033456 A1 | 2/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039876 A1 | 2/2008 | Catanese et al. |
| 2008/0039889 A1 | 2/2008 | Lamson et al. |
| 2008/0039893 A1 | 2/2008 | McLean et al. |
| 2008/0039894 A1 | 2/2008 | Catanese et al. |
| 2008/0045986 A1 | 2/2008 | To et al. |
| 2008/0051756 A1 | 2/2008 | Makower et al. |
| 2008/0058759 A1 | 3/2008 | Makower et al. |
| 2008/0071341 A1 | 3/2008 | Goode et al. |
| 2008/0071342 A1 | 3/2008 | Goode et al. |
| 2008/0097426 A1 | 4/2008 | Root et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0125748 A1 | 5/2008 | Patel |
| 2008/0147061 A1 | 6/2008 | Goode et al. |
| 2008/0154293 A1 * | 6/2008 | Taylor .............. 606/170 |
| 2008/0154296 A1 | 6/2008 | Taylor et al. |
| 2008/0183163 A1 | 7/2008 | Lampropoulos et al. |
| 2008/0208105 A1 | 8/2008 | Zelickson et al. |
| 2008/0221560 A1 | 9/2008 | Arai et al. |
| 2008/0228208 A1 | 9/2008 | Wulfman et al. |
| 2008/0249516 A1 | 10/2008 | Muenker |
| 2008/0262516 A1 | 10/2008 | Gambale et al. |
| 2008/0275497 A1 | 11/2008 | Palmer et al. |
| 2008/0275498 A1 | 11/2008 | Palmer et al. |
| 2008/0281308 A1 | 11/2008 | Neuberger et al. |
| 2008/0287888 A1 | 11/2008 | Ravenscroft |
| 2008/0306333 A1 | 12/2008 | Chin |
| 2009/0012510 A1 | 1/2009 | Bertolero et al. |
| 2009/0018523 A1 | 1/2009 | Lamson et al. |
| 2009/0018553 A1 | 1/2009 | McLean et al. |
| 2009/0034927 A1 | 2/2009 | Temelkuran et al. |
| 2009/0036871 A1 | 2/2009 | Hayase et al. |
| 2009/0054918 A1 | 2/2009 | Henson |
| 2009/0060977 A1 | 3/2009 | Lamson et al. |
| 2009/0071012 A1 | 3/2009 | Shan et al. |
| 2009/0076522 A1 | 3/2009 | Shan |
| 2009/0131907 A1 | 5/2009 | Chin et al. |
| 2009/0157045 A1 | 6/2009 | Haarala et al. |
| 2009/0192439 A1 | 7/2009 | Lamson et al. |
| 2009/0204128 A1 | 8/2009 | Lamson et al. |
| 2009/0221994 A1 | 9/2009 | Neuberger et al. |
| 2009/0222025 A1 | 9/2009 | Catanese et al. |
| 2009/0227999 A1 | 9/2009 | Willis et al. |
| 2009/0234378 A1 | 9/2009 | Escudero et al. |
| 2009/0270862 A1 | 10/2009 | Arcenio |
| 2010/0004606 A1 | 1/2010 | Hansen et al. |
| 2010/0030154 A1 | 2/2010 | Duffy |
| 2010/0030161 A1 | 2/2010 | Duffy |
| 2010/0030262 A1 | 2/2010 | McLean et al. |
| 2010/0030263 A1 | 2/2010 | Cheng et al. |
| 2010/0049225 A1 | 2/2010 | To et al. |
| 2010/0063488 A1 | 3/2010 | Fischer et al. |
| 2010/0125253 A1 | 5/2010 | Olson et al. |
| 2010/0137873 A1 | 6/2010 | Grady et al. |
| 2010/0160952 A1 | 6/2010 | Leeflang et al. |
| 2010/0191165 A1 | 7/2010 | Appling et al. |
| 2010/0198194 A1 | 8/2010 | Manning et al. |
| 2010/0198229 A1 | 8/2010 | Olomutzki et al. |
| 2010/0217081 A1 | 8/2010 | Deppmeier et al. |
| 2010/0217277 A1 | 8/2010 | Truong |
| 2010/0222737 A1 | 9/2010 | Arnold et al. |
| 2010/0222787 A1 | 9/2010 | Goode et al. |
| 2010/0240951 A1 | 9/2010 | Catanese et al. |
| 2010/0256616 A1 | 10/2010 | Katoh et al. |
| 2010/0280496 A1 | 11/2010 | Shippert |
| 2010/0324472 A1 | 12/2010 | Wulfman |
| 2010/0331793 A1 | 12/2010 | Tulleken |
| 2011/0004238 A1 | 1/2011 | Palmer et al. |
| 2011/0009957 A1 | 1/2011 | Langberg et al. |
| 2011/0022057 A1 | 1/2011 | Eigler et al. |
| 2011/0028959 A1 | 2/2011 | Chasan |
| 2011/0034790 A1 | 2/2011 | Mourlas et al. |
| 2011/0040238 A1 | 2/2011 | Wulfman et al. |
| 2011/0040312 A1 | 2/2011 | Lamson et al. |
| 2011/0040315 A1 | 2/2011 | To et al. |
| 2011/0040326 A1 | 2/2011 | Wei et al. |
| 2011/0046648 A1 | 2/2011 | Johnston et al. |
| 2011/0054493 A1 | 3/2011 | McLean et al. |
| 2011/0060349 A1 | 3/2011 | Cheng et al. |
| 2011/0071440 A1 | 3/2011 | Torrance et al. |
| 2011/0105947 A1 | 5/2011 | Fritscher-Ravens et al. |
| 2011/0106004 A1 | 5/2011 | Eubanks et al. |
| 2011/0106099 A1 | 5/2011 | Duffy et al. |
| 2011/0112548 A1 | 5/2011 | Fifer et al. |
| 2011/0112562 A1 | 5/2011 | Torrance |
| 2011/0112563 A1 | 5/2011 | To et al. |
| 2011/0112564 A1 | 5/2011 | Wolf |
| 2011/0118660 A1 | 5/2011 | Torrance et al. |
| 2011/0144423 A1 | 6/2011 | Tong et al. |
| 2011/0144425 A1 | 6/2011 | Catanese et al. |
| 2011/0151463 A1 | 6/2011 | Wulfman |
| 2011/0152607 A1 | 6/2011 | Catanese et al. |
| 2011/0152906 A1 | 6/2011 | Escudero et al. |
| 2011/0152907 A1 | 6/2011 | Escudero et al. |
| 2011/0160747 A1 | 6/2011 | McLean et al. |
| 2011/0160748 A1 | 6/2011 | Catanese et al. |
| 2011/0166564 A1 | 7/2011 | Merrick et al. |
| 2011/0178543 A1 | 7/2011 | Chin et al. |
| 2011/0190758 A1 | 8/2011 | Lamson et al. |
| 2011/0196298 A1 | 8/2011 | Anderson et al. |
| 2011/0196355 A1 | 8/2011 | Mitchell et al. |
| 2011/0208207 A1 | 8/2011 | Bowe et al. |
| 2011/0213398 A1 | 9/2011 | Chin et al. |
| 2011/0218528 A1 | 9/2011 | Ogata et al. |
| 2011/0238078 A1 | 9/2011 | Goode et al. |
| 2011/0238102 A1 | 9/2011 | Gutfinger et al. |
| 2011/0245751 A1 | 10/2011 | Hofmann |
| 2011/0257592 A1 | 10/2011 | Ventura et al. |
| 2011/0270169 A1 | 11/2011 | Gardeski et al. |
| 2011/0270170 A1 | 11/2011 | Gardeski et al. |
| 2011/0270289 A1 | 11/2011 | To et al. |
| 2011/0300010 A1 | 12/2011 | Jarnagin et al. |
| 2011/0301417 A1 | 12/2011 | Mourlas et al. |
| 2011/0301626 A1 | 12/2011 | To et al. |
| 2012/0029278 A1 | 2/2012 | Sato et al. |
| 2012/0035590 A1 | 2/2012 | Whiting et al. |
| 2012/0041422 A1 | 2/2012 | Whiting et al. |
| 2012/0053564 A1 | 3/2012 | Ravenscroft |
| 2012/0065659 A1 | 3/2012 | To |
| 2012/0083810 A1 | 4/2012 | Escudero et al. |
| 2012/0083826 A1 | 4/2012 | Chao et al. |
| 2012/0095447 A1 | 4/2012 | Fojtik |
| 2012/0095479 A1 | 4/2012 | Bowe et al. |

(56) References Cited

U.S. PATENT DOCUMENTS

| | | |
|---|---|---|
| 2012/0097174 A1 | 4/2012 | Spotnitz et al. |
| 2012/0123411 A1 | 5/2012 | Ibrahim et al. |
| 2012/0136341 A1 | 5/2012 | Appling et al. |
| 2012/0165827 A1 | 6/2012 | Khairkhahan et al. |
| 2012/0165861 A1 | 6/2012 | Palmer et al. |
| 2012/0191015 A1 | 7/2012 | Zannis et al. |
| 2012/0209173 A1 | 8/2012 | Hayase et al. |
| 2012/0215305 A1 | 8/2012 | Le et al. |
| 2012/0239008 A1 | 9/2012 | Fojtik |
| 2012/0245600 A1 | 9/2012 | McLean et al. |
| 2012/0253229 A1 | 10/2012 | Cage |
| 2012/0265183 A1 | 10/2012 | Tulleken et al. |
| 2012/0323252 A1 | 12/2012 | Booker |
| 2012/0323253 A1 | 12/2012 | Garai et al. |
| 2012/0330292 A1 | 12/2012 | Shadduck et al. |
| 2013/0006228 A1 | 1/2013 | Johnson et al. |
| 2013/0035676 A1 | 2/2013 | Mitchell et al. |
| 2013/0096582 A1 | 4/2013 | Cheng et al. |
| 2013/0103047 A1 | 4/2013 | Steingisser et al. |
| 2015/0105796 A1 | 4/2015 | Grace |

FOREIGN PATENT DOCUMENTS

| | | |
|---|---|---|
| WO | 9117711 A1 | 11/1991 |
| WO | 9533513 A1 | 12/1995 |
| WO | 9907295 A1 | 2/1999 |
| WO | 9949937 A1 | 10/1999 |
| WO | 9958066 A1 | 11/1999 |
| WO | 0176680 A1 | 10/2001 |
| WO | 0249690 A9 | 5/2003 |
| WO | 2004049956 A2 | 6/2004 |
| WO | 2004080345 A2 | 9/2004 |
| WO | 2004080507 A2 | 9/2004 |
| WO | 2006007410 A2 | 1/2006 |
| WO | 2008005888 A2 | 1/2008 |
| WO | 2008005891 A2 | 1/2008 |
| WO | 2008042987 A2 | 4/2008 |
| WO | 2009005779 A1 | 1/2009 |
| WO | 2009054968 A1 | 4/2009 |
| WO | 2009065082 A1 | 5/2009 |
| WO | 2009126309 A2 | 10/2009 |
| WO | 2011003113 A1 | 1/2011 |
| WO | 2011084863 A2 | 7/2011 |
| WO | 2011133941 A2 | 10/2011 |
| WO | 2011162595 A1 | 12/2011 |
| WO | 2012009697 A4 | 4/2012 |
| WO | 2012098335 A1 | 7/2012 |
| WO | 2012114333 A1 | 8/2012 |
| WO | 2012177117 A1 | 12/2012 |
| WO | 2013036588 A1 | 3/2013 |
| WO | 2014151814 A1 | 9/2014 |

OTHER PUBLICATIONS

U.S. Appl. No. 62/113,865 entitled Medical Device for Removing an Implanted Object, filed Feb. 9, 2015.
Decision to Grant for European Patent Application No. 07255018.9, dated Aug. 8, 2013, 2 pages.
U.S. Appl. No. 62/058,790 entitled Medical Device for Removing an Implanted Object, filed Oct. 2, 2014.
EP extended Search Report mailed Oct. 21, 2009; Application No. 07255019.7, 8 pages.
Extended European Search Report for European Application No. 07255018.9, dated Nov. 12, 2010.
Final Action for U.S. Appl. No. 11/615,005, mailed Nov. 9, 2009, 10 pages.
Final Action for U.S. Appl. No. 11/615,005, mailed Nov. 21, 2013, 20 pages.
Intent to Grant for European Patent Application No. 07255018.9, dated Nov. 29, 2012, 7 pages.
International Search Report and Written Opinion for International Patent Application No. PCT/US2013/059434, dated Dec. 13, 2013, 14 pages.
International Search Report and Written Opinion issued in PCT/US2014/021167 mailed Jun. 26, 2014, 19 pages.
International Search Report and Written Opinion issued in PCT/US2014/026496 mailed Jul. 30, 2014, 16 pages.
International Search Report and Written Opinion issued in PCT/US2015/016899, mailed May 1, 2015.
International Search Report and Written Opinion issued in PCT/US2015/016899, mailed May 1, 2015, 14 pages.
International Search Report and Written Opinion issued in PCT/US2015/018305, mailed May 28, 2015, 14 pages.
Notice of Allowance for European Patent Application No. 07255018.9, dated Jul. 26, 2012, 47 pages.
Notice of Allowance for Japan Patent Application No. 2007-333273, mailed Jan. 16, 2014, 3 pages.
Official Action for European Patent Application No. 07255018.9, dated Jul. 19, 2011, 3 pages.
Official Action for U.S. Appl. No. 11/615,005, mailed Apr. 16, 2009, 13 pages.
Official Action for U.S. Appl. No. 11/615,005, mailed Feb. 11, 2011, 12 pages.
Official Action for U.S. Appl. No. 11/615,005, mailed Jul. 21, 2010, 10 pages.
Official Action for U.S. Appl. No. 11/615,005, mailed Mar. 14, 2013, 16 pages.
Official Action for U.S. Appl. No. 13/800,728, mailed Jan. 16, 2014, 14 pages.
Official Action with English translation for Japan Patent Application No. 2007-333173, mailed Apr. 30, 2013, 5 pages.
Official Action with English translation for Japan Patent Application No. 2007-333173, mailed Aug. 13, 2012, 7 pages.
Official Action with English translation for Japan Patent Application No. 2007-333273, mailed Jul. 30, 2012, 7 pages.
Official Action with English translation for Japan Patent Application No. 2007-333273, mailed Jun. 6, 2013, 10 pages.
PCT Application No. PCT/US2015/016899 entitled Medical Device for Removing an Implanted Object filed Feb. 20, 2015.
PCT Application No. PCT/US2015/018305 entitled Multiple Configuration Surgical Cutting Device filed Mar. 2, 2015.
U.S. Appl. No. 13/800,651 entitled System and Method of Ablative Cutting and Pulsed Vacuum Aspiration, filed Mar. 13, 2013.
U.S. Appl. No. 13/800,675 entitled Laser Catheter With Helical Internal Lumen, filed Mar. 13, 2013.
U.S. Appl. No. 13/800,700 entitled Device and Method of Ablative Cutting With Helical Tip, filed Mar. 13, 2013.
U.S. Appl. No. 13/800,728 entitled Laser Ablation Catheter, filed Mar. 13, 2013.
U.S. Appl. No. 13/828,231 entitled Tissue Slitting Methods and Systems, filed Mar. 14, 2013.
U.S. Appl. No. 13/828,310 entitled Tissue Slitting Methods and Systems, filed Mar. 14, 2013.
U.S. Appl. No. 13/828,383 entitled Tissue Slitting Methods and Systems, filed Mar. 14, 2013.
U.S. Appl. No. 13/828,441 entitled Tissue Slitting Methods and Systems, filed Mar. 14, 2013.
U.S. Appl. No. 13/828,536 entitled Expandable Lead Jacket, filed Mar. 14, 2013.
U.S. Appl. No. 13/828,638 entitled Lead Removal Sleeve, filed Mar. 14, 2013.
U.S. Appl. No. 13/834,405 entitled Retractable Blade for Lead Removal Device, filed Mar. 15, 2013.
U.S. Appl. No. 14/577,976 entitled Surgical Instrument Including an Inwardly Deflecting Cutting Tip for Removing an Implanted Object, filed Dec. 19, 2014.
U.S. Appl. No. 14/589,688 entitled Retractable Separating Systems and Methods, filed Jan. 5, 2015.
U.S. Appl. No. 14/627,851 entitled Medical Device for Removing an Implanted Object, filed Feb. 20, 2015.
U.S. Appl. No. 14/627,950 entitled Medical Device for Removing an Implanted Object, filed Feb. 20, 2015.
U.S. Appl. No. 14/635,742 entitled Multiple Configuration Surgical Cutting Device, filed Mar. 2, 2015.
U.S. Design Application No. 29/519,239 entitled Medical Device Handle, filed Mar. 3, 2015.

(56) References Cited

OTHER PUBLICATIONS

U.S. Design Application No. 29/519,258 entitled Medical Device Handle, filed Mar. 3, 2015.
U.S. Appl. No. 14/725,781, filed May 29, 2015, entitled Surgical Instrument for Removing an Implanted Object.
U.S. Appl. No. 61/793,597 entitled Surgical Instrument for Removing an Implanted Object, filed Mar. 15, 2013.
U.S. Appl. No. 61/987,993 entitled Dual Mode Mechanical Catheter Cutting System, filed May 2, 2014.
U.S. Appl. No. 62/005,315 entitled Surgical Instrument for Removing an Implanted Object, filed May 30, 2014.

* cited by examiner

ALARM FOR LEAD INSULATION ABNORMALITY

CROSS REFERENCE TO RELATED APPLICATION

Not applicable.

FIELD

The disclosure relates generally to surgical implants and particularly to installation and/or removal of surgical implants.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure every 5 to 10 years. The other parts are the wires, or leads, which run between the pulse generator and the heart. In a pacemaker, these leads allow the device to increase the heart rate by delivering small timed bursts of electric energy to make it beat faster. In a defibrillator, the lead has special coils to allow the device to deliver a high-energy shock and convert dangerous rapid rhythms (ventricular tachycardia or fibrillation) back to a normal rhythm. The leads transmit information about the heart's electrical activity to the pacemaker.

For both of these functions, leads must be in contact with heart tissue. Most leads pass through a vein under the collarbone that connects to the right side of the heart (right atrium and right ventricle). In some cases, a lead is inserted through a vein and guided into a heart chamber where it is attached with the heart. In other instances, a lead is attached to the outside of the heart. To remain attached to the heart muscle, most leads have a fixation mechanism, such as a small screw and/or hooks at the end. Within a few months, the body's natural healing process forms scar tissue along the lead and at its tip, which fastens it even more securely in the patient's body, thereby complicating removal or extraction of the pacing lead. Leads usually last longer than device batteries, so leads are simply reconnected to each new pulse generator (battery) at the time of replacement.

Although leads are designed to be implanted permanently in the body, occasionally these leads must be removed, or extracted. The most common reason for lead extraction is infection. If any part of the system becomes infected, it is usually impossible to cure the infection without completely removing all hardware from the body. This requires removal both of the pulse generator form the chest wall and all leads from the veins and heart. Another reason for lead extraction is when a lead fails to work properly (for example, due to a break in the metal wire or surrounding insulation). Sometimes, the broken lead can be abandoned in the heart, with a new lead placed alongside. However, veins can only accommodate a limited number of leads due to space constraints, and sometimes, nonfunctioning leads must be extracted to make space for a new lead.

A variety of tools have been developed to make lead extraction safer and more successful. Current pacing lead extraction techniques include mechanical traction, mechanical devices, and energy devices. Some mechanical devices use a wire that passes down the length of the lead, locking into place and allowing force to be applied to the tip of the lead. Another mechanical tool is a flexible tube called a sheath that passes over the lead, surrounding it and freeing it from the body by disrupting scar tissue as it is advanced toward the heart. Another mechanical tool uses a mechanical cutter to break through the scar tissue. Dilating telescopic sheaths can be used to strip or push away the scar tissue adhering the lead to the body. Energy devices, known as power sheaths, typically apply a form of energy at the sheath tip to cut the scar tissue away from the lead thus allowing for removal. As the sheath is pushed over the lead and comes to an area of attachment, the operator can turn on the sheath's energy source to heat or vaporize scar tissue. This has the effect of cutting the lead from its attachments, allowing the lead to be removed safely with much less force. One of these specialized sheaths uses electrocautery, similar to what is used to cut through tissue in surgery. Another commonly used sheath has a ring of tiny lasers at its tip. When activated, the lasers vaporize water molecules in scar tissue within 1 mm, which allows the sheath to be passed slowly over the entire lead until it can be removed. Occasionally, leads cannot be extracted from the chest and are instead removed through the femoral vein in the groin by use of specialized tools.

In any of the above lead removal devices and techniques, a damaged outer insulation layer of the lead can weaken the lead, which is often under significant tension or pull forces needed to assist its removal. In addition to lead damage from defective manufacture or lead implantation, leads can be perforated or cut during lead removal. Once the lead insulation layer is compromised, the remaining insulation layer can tear, and the inner conductive structures unravel.

SUMMARY

These and other needs are addressed by the various aspects, embodiments, and configurations of the present disclosure.

A device, described in this disclosure, can include:

(a) a separator to substantially free an implanted lead from surrounding tissue;

(b) a sensor to sense an electrical parameter associated with the lead to determine a condition of an insulation layer of the lead; and (c) a controller operable to receive output from the sensor and determine when the condition of the insulation layer is not acceptable.

A method, described in this disclosure, can include the steps of:

(a) detecting an irregularity in an insulating layer of an implanted lead; and (b) warning a physician of the irregularity.

A non-transient, tangible computer readable medium is described comprising microprocessor executable instructions that, when executed by a microprocessor, perform the following steps:

(a) receiving, by a controller and from a sensor, a sensed electrical parameter associated with an implanted lead;

(b) comparing, by the controller, the sensed electrical parameter with one or more predetermined thresholds associated with the existence of an irregularity; and (c) based on the comparing step, determining, by the controller, that the implanted lead has an irregularity.

A system, described in this disclosure, can include:

(a) an electrically conductive structure operable to provide, in the event of an irregularity in an insulating layer of an implanted lead, a changed electrical parameter associated with the lead;

(b) a sensor operable to sense the changed electrical parameter; and (c) a controller operable to determine an instance of an irregularity in the lead based on the sensed, changed electrical parameter and warn a physician of the determined instance of an irregularity.

A sheath can be used in the detection of an irregularity. The sheath can include an annulus to receive the implanted lead and the electrically conductive structure to interact electrically with a conductor of the lead when the condition of the insulation layer is not acceptable. The electrically conductive structure can be configured as one or more conductive band(s) around at least part of a circumference of the sheath.

The sheath can further include a marker in spatial proximity to the electrically conductive structure to indicate a location, in a body of a patient, of an unacceptable portion of the insulation layer.

The present disclosure can provide a number of advantages depending on the particular configuration. The various devices discussed in the present disclosure can readily, conveniently, accurately, and quickly detect and notify a physician of a damaged outer insulation layer of a lead. The physician can therefore take remedial action to avoid injuring the patient.

These and other advantages will be apparent from the disclosure of the aspects, embodiments, and configurations contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The term "computer-readable medium" as used herein refers to any storage and/or transmission medium that participate in providing instructions to a processor for execution. Such a medium is commonly tangible and non-transient and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

The terms "determine", "calculate" and "compute," and variations thereof, as used herein, are used interchangeably and include any type of methodology, process, mathematical operation or technique.

A "lead" is a conductive structure, typically an electrically insulated coiled wire. The electrically conductive material can be any conductive material, with metals and intermetallic alloys common. The outer sheath of insulative material is biocompatible and biostable (e.g., non-dissolving in the body) and generally includes organic materials such as polyurethane and polyimide. Lead types include, by way of non-limiting example, epicardial and endocardial leads. Leads are commonly implanted into a body percutaneously or surigically.

A "surgical implant" is a medical device manufactured to replace a missing biological structure, support, stimulate, or treat a damaged biological structure, or enhance, stimulate, or treat an existing biological structure. Medical implants are man-made devices, in contrast to a transplant, which is a transplanted biomedical tissue. In some cases implants contain electronics, including, without limitation, artificial pacemaker, defibrillator, electrodes, and cochlear implants. Some implants are bioactive, including, without limitation, subcutaneous drug delivery devices in the form of implantable pills or drug-eluting stents.

The term "means" as used herein shall be given its broadest possible interpretation in accordance with 35 U.S.C. Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "module" as used herein refers to any known or later developed hardware, software, firmware, artificial intelligence, fuzzy logic, or combination of hardware and software that is capable of performing the functionality associated with that element. Also, while the disclosure is presented in terms of exemplary embodiments, it should be appreciated that individual aspects of the disclosure can be separately claimed.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Embodiments according to this disclosure provide a catheter sheath assembly that can be deployed safely within a vascular system of a patient. A catheter sheath assembly can include, for example, a flexible sheath coupled with a separator to separate a lead from adjoining or adjacent scar tissue. The separator can use any separation mechanism, or lead extraction technique, including mechanical traction, a mechanical device, and/or an energy device. An exemplary separator includes one or more cutting elements, cutting assemblies, cutters, stripping elements, strippers, dilating elements, dilaters, lasers, and the like.

Figure 1:
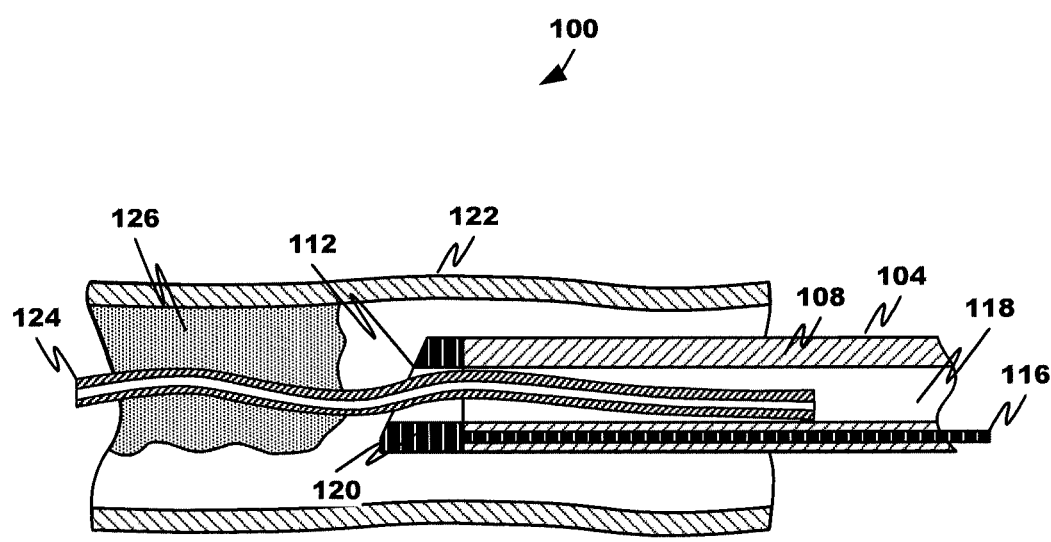
FIG. 1 is a cross-sectional view of a sheath assembly removing a lead according to an embodiment of the disclosure.
Figure 2:
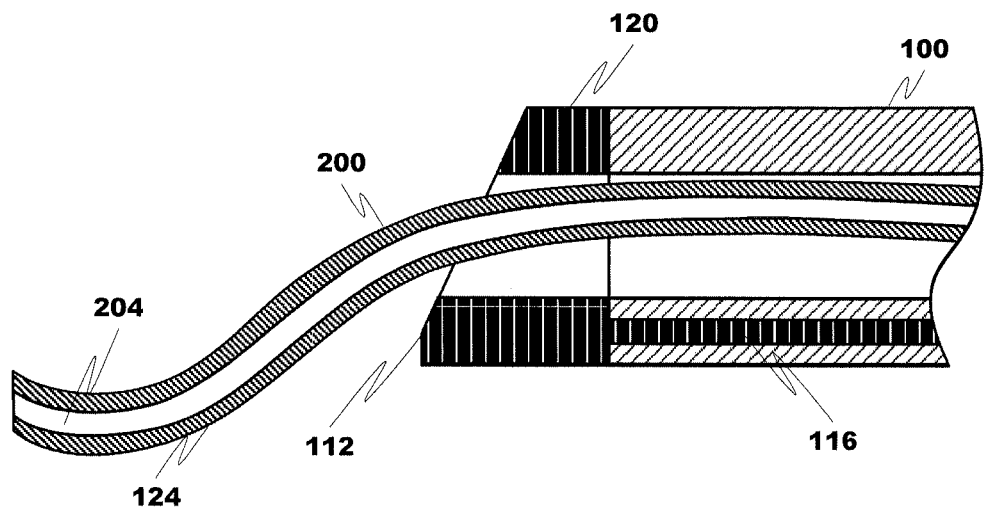
FIG. 2 is a cross-sectional view of the sheath assembly of FIG. 1.
Figure 3:
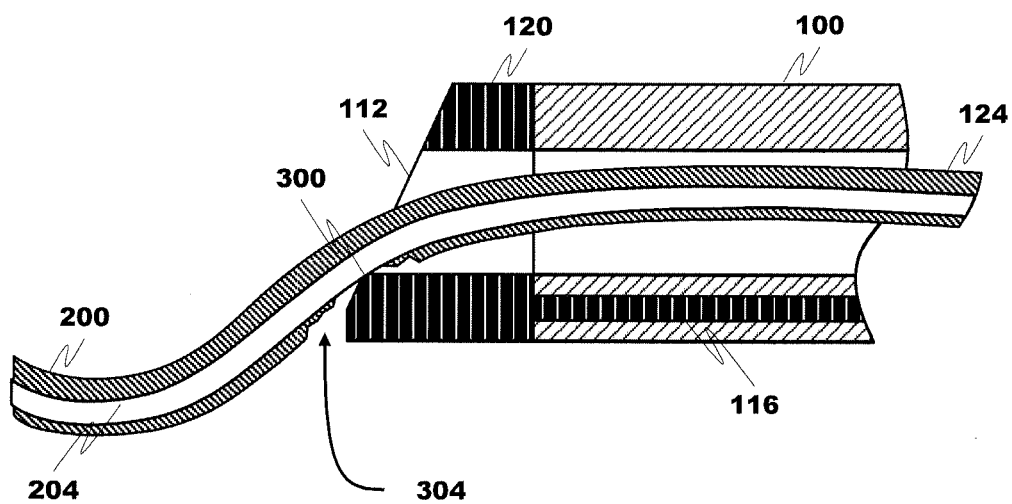
FIG. 3 is a cross-sectional view of the sheath assembly of FIG. 2.

With reference to FIGS. 1-3, an exemplary catheter sheath assembly 100 is depicted. The sheath assembly comprises a flexible cylindrical or tubular body member 104 having a distal tip 112 and separator (not shown) at its distal end, a handle (not shown) at is proximal end, an intervening substantially cylindrical sidewall 108, and one or more markers or other detectable features that can be imaged. The sidewall comprises a longitudinal electrical conductive element 116 in electrical communication with a circumferential electrical conductive element 120. The longitudinal and circumferential electrical conductive elements 116 and 120, respectively, are composed of a highly conductive material, such as a metal or intermetallic alloy. The conductive material may be the same as or different from the conductive material in the lead 124. The annulus 118 defined by the sidewall 108 receives the lead 124.

The portions of the sidewall 108 between the longitudinal and circumferential electrical conductive elements 116 and 120, respectively, are typically composed of a biocompatible, biostable, and substantially non-conducting material, such as an organic polymeric material. For example, it may have the same or different composition as the insulation layer of the lead 124. The portions of the sidewall may be manufactured from a flexible polymer such as Pebax™ or Teflon™. The longitudinal and circumferential conductive elements 116 and 120 may be configured as a reinforcement to the structural integrity or strength of the sheath assembly, such as a stainless steel reinforcement.

The sheath assembly 100 and lead 124 are positioned within a vasculature 122, with a portion of the lead 124 being positioned in the annulus 118 of the sheath assembly 100. The sheath assembly 100 is advancing to cut a tissue growth 126 obstructing removal of the lead 124. The lead 124 comprises an insulating layer or lead insulation material 200 positioned around the circumference of one or more conductive elements 204.

FIG. 3 depicts the distal tip 112 nicking or cutting the insulating layer 200 of the lead 124 to form damaged portion 304 of the lead insulation, thereby exposing the enclosed conductive elements 204 in the vasculature 122. As will be appreciated, not only can the damaged portion 304 compromise the structural integrity of the lead 124 during removal but also the exposed conductors can puncture or otherwise wound the surrounding tissue of the patient.

The direct electrical contact of the exposed conductors and the circumferential conductive element 120 can be detected by measuring an electrical parameter associated with either the sheath assembly 100 or lead 124, as discussed more fully below.

Figure 8:
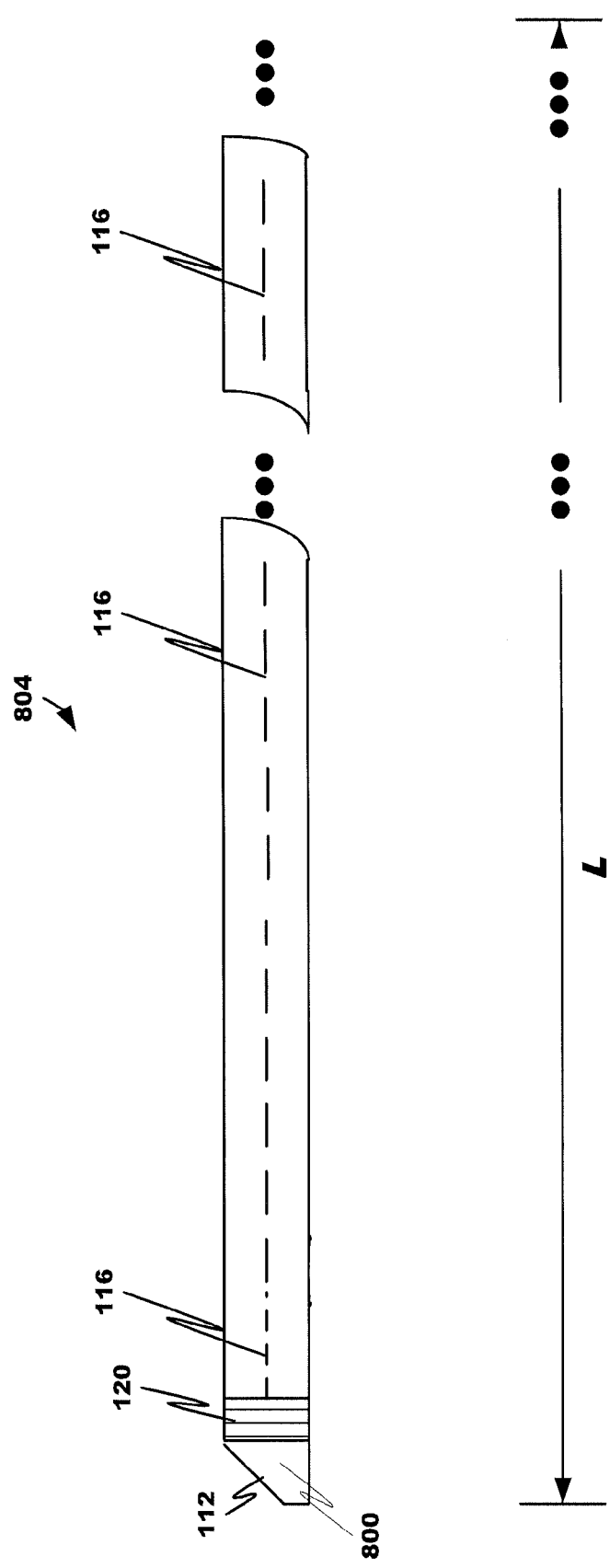
FIG. 8 depicts a side view of a sheath assembly according to an embodiment of the disclosure.

Referring to FIG. 8, another exemplary sheath assembly 804 is depicted. The sheath assembly 804 comprises longitudinal and circumferential conductive members 116 and 120, respectively, with the circumferential conductive member 120 being located proximal to the distal tip 112. The longitudinal electrical conductive element 116 extends substantially the entire length ("L") of the sheath assembly 704 while the circumferential electrical conductive element 120 extends substantially the entire diameter of the sheath assembly 704. The sheath assembly 100 further comprises a marker 800 on the distal tip 112 to enable locating the distal tip 112 in the patient body. This can enable a physician to locate abnormalities in the insulating layer of a lead as the distal tip 112 transgresses the length of the lead.

Figure 9:
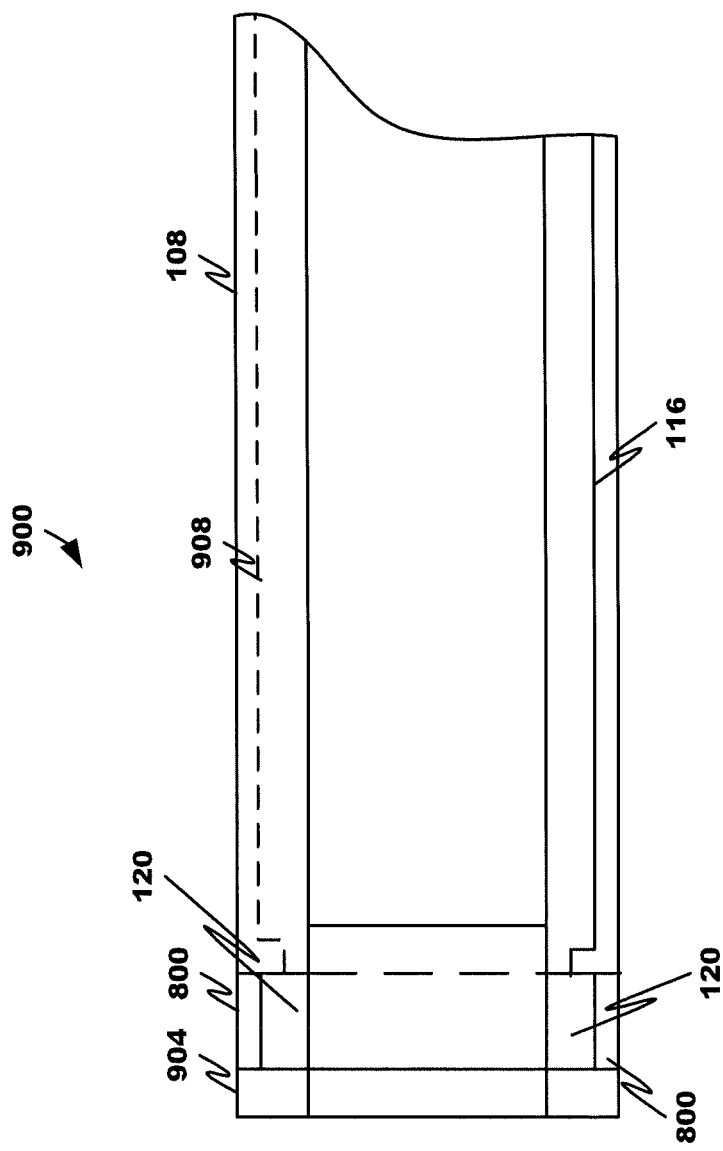
FIG. 9 depicts a cross-sectional side view of a sheath assembly according to an embodiment of the disclosure.

Referring to FIG. 9, another exemplary sheath assembly 900 is depicted. The sheath assembly 900 comprises a separator 904, a marker 800, and the longitudinal and circumferential conductive members 116 and 120. An optional second longitudinal conductive member 908 may be provided as discussed more fully below. As will be appreciated, the relative positions of the circumferential conductive member 116 and marker 800 can be reversed, with the marker 800 being positioned below the circumferential conductive member 120.

The markers or other detectable feature(s) can include a tip marker (shown), a separator marker (not shown), or a sheath marker (not shown), or any combination thereof. Such markers may include a radiopaque or other imageable material to allow an operator to determine the relative positional relationships of the separator 904. In some cases, the components of the separator 904 can be constructed of radiopaque material or alternatively plated with a thin coat of highly radiopaque material such as gold. In one embodiment, a tip marker includes a radiopaque material that allows the operator to determine a position of the distal tip and/or other portion(s) of the sheath assembly in the body of the patient.

Figure 7:
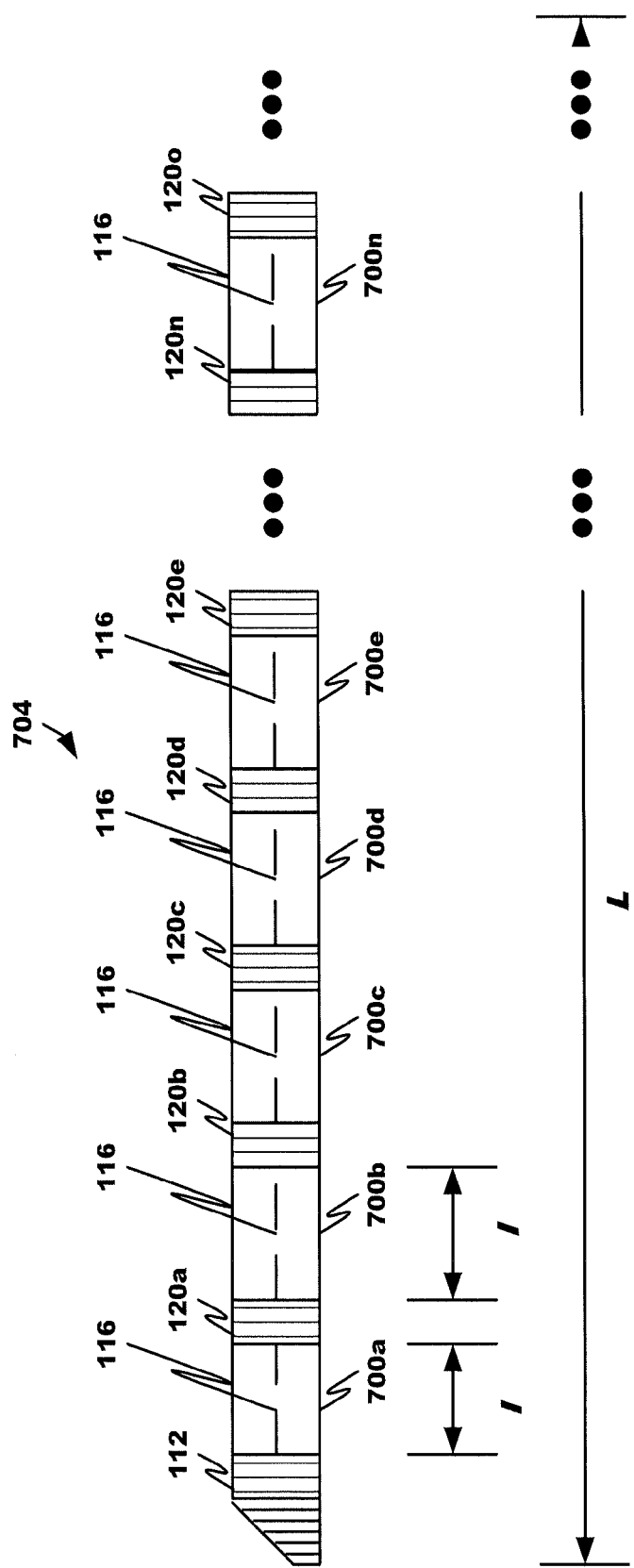
FIG. 7 depicts a side view of a sheath assembly according to an embodiment of the disclosure.

Referring to FIG. 7, yet another exemplary sheath assembly 704 is depicted. Multiple circumferential electrical conductive elements 120a-o may be positioned at determined intervals ("I") along the length "L" of the sheath assembly 704. The intervals "I" may be uniform or non-uniform depending on the application. Commonly and as shown in FIG. 7, the spacing or intervals "I" between adjacent circumferential electrical conductive elements is small enough that any point along substantially the entire length of the conductive element(s) in the lead 124, in the event of damage to the outer insulation layer, is in electrical communication with one or more adjacent circumferential electrical conductive element(s) 120a-o. This sheath configuration has the advantage that damage to the lead during removal from a cause other than contact with the separator 904 can be readily detected by the plural circumferential electrical conductive elements 120.

A number of operational modes will now be discussed.

Figure 10:
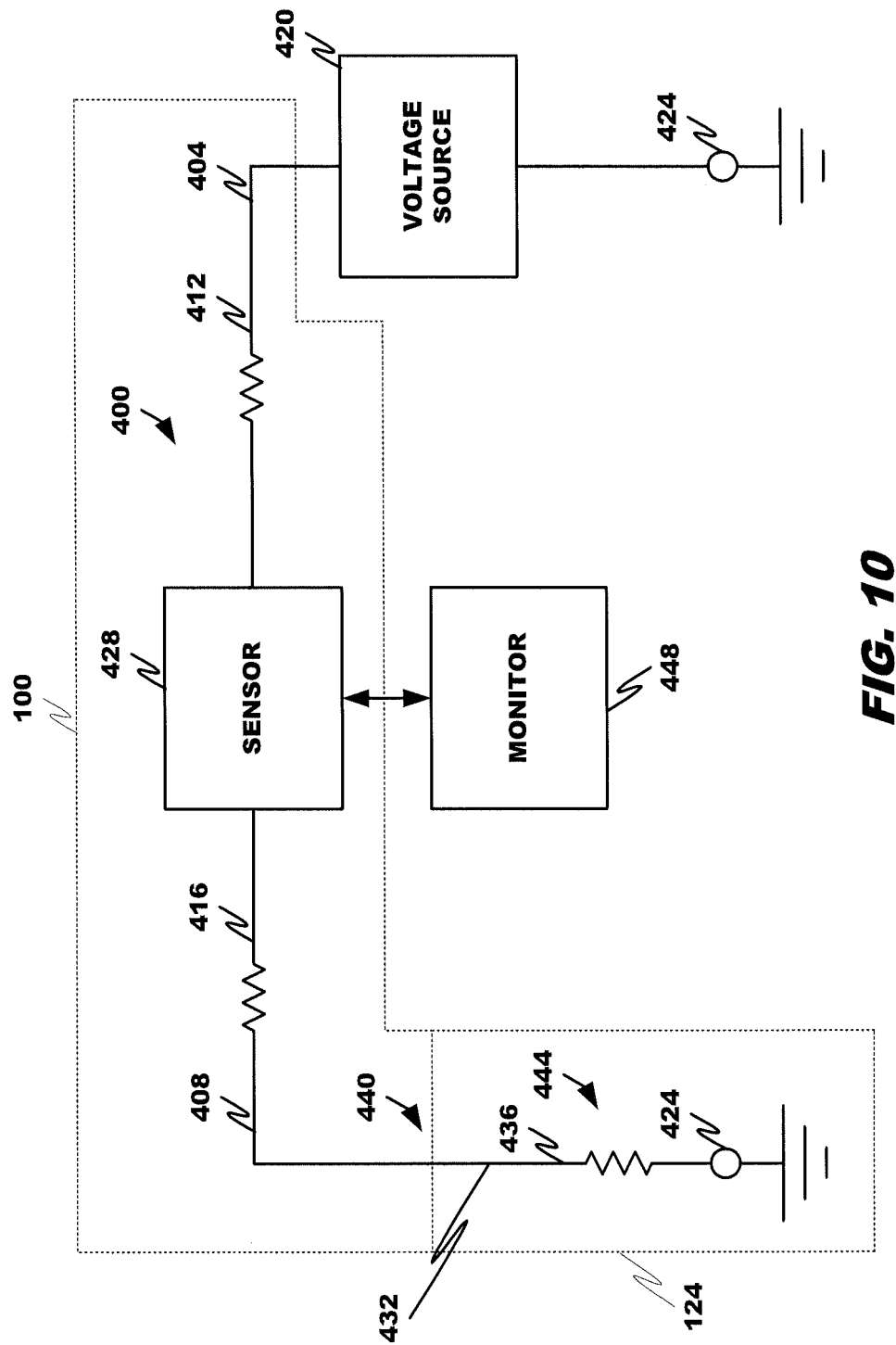
FIG. 10 is an electrical schematic according to an embodiment of the disclosure.

FIG. 10 depicts a first operating mode according to the disclosure. An electrical circuit defined by the circumferential and longitudinal conductive elements of the sheath assembly 100 is shown. The circuit 400 comprises conductors 404 and 408, each having internal resistance 412 and 416, respectively, electrically connected to a terminal of a voltage source 420 (which may be a direct or alternating current and fixed or variable voltage source) and sensor 428. The other terminal of the voltage source 420 is electrically connected to ground 424. The sensor 428 can measure one or more electrical parameters, including voltage, current and resistance.

Typical sensors 428 comprise ammeters, ohmmeters, voltmeters, potentiometer, oscilloscope, and the like. The circuit 444 of the lead 124 comprises a conductor 432 having internal resistance 436 connected electrically to ground 424. A direct electrical connection, such as shown in FIG. 3, exists between the circuits 400 and 444, thereby enabling electrical current to flow between the circuits. The sensor 428 is electrically connected to circuit 400 but may, alternatively, be electrically connected to the circuit 444.

Figure 11:
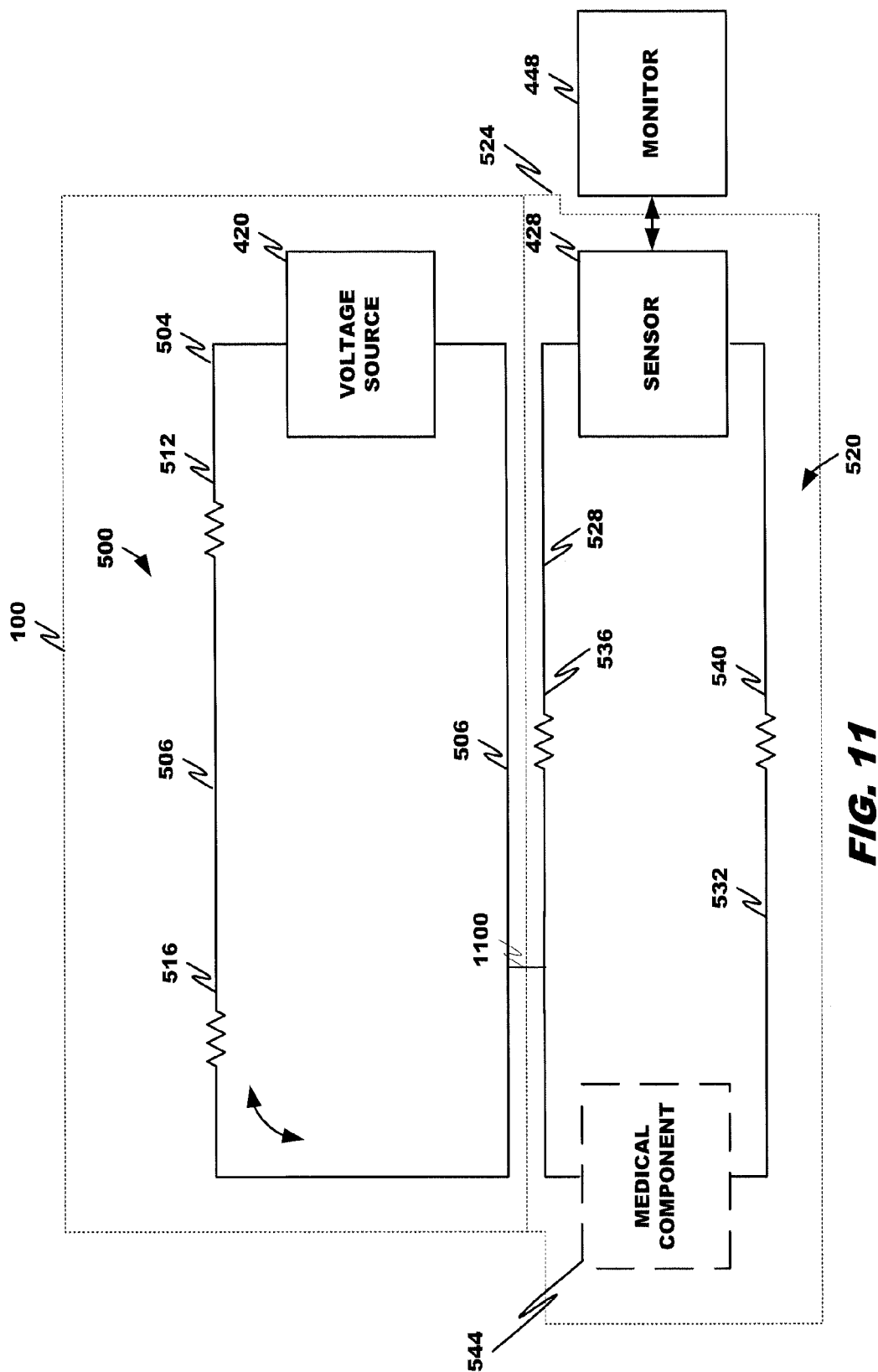
FIG. 11 is an electrical schematic according to an embodiment of the disclosure.

FIG. 11 depicts a second operating mode according to the disclosure. An electrical circuit defined by the circumferential and longitudinal conductive elements of the sheath assembly 100 is shown. The circuit 500 comprises conductors 504, 506, and 508, having internal resistance 512 and 516, respectively, electrically connected to a terminal of a voltage source 420. Electrical current can flow either clockwise or counterclockwise, as shown. Unlike the prior operational mode, the circuit 500 is closed while the circuit 400 is open. The circuit 520 of the lead 524 comprises conductors 528 and 532 having internal resistance 536 and 540, respectively. The conductors 528 in the lead 524 can be optionally connected to an implanted medical component 544, such as a cardiac pacing system, or, in the event that the medical component 544 has been removed or not yet implanted, to one another or disconnected altogether. The conductors 528 and 540 are further connected to the sensor 428 to form a closed circuit, unlike the typically open circuit 444 of FIG. 4. As shown by connection 1100, a direct electrical connection, such as shown in FIG. 3, exists between the circuits 500 and 520, thereby enabling electrical current to flow between the circuits.

Figure 4:
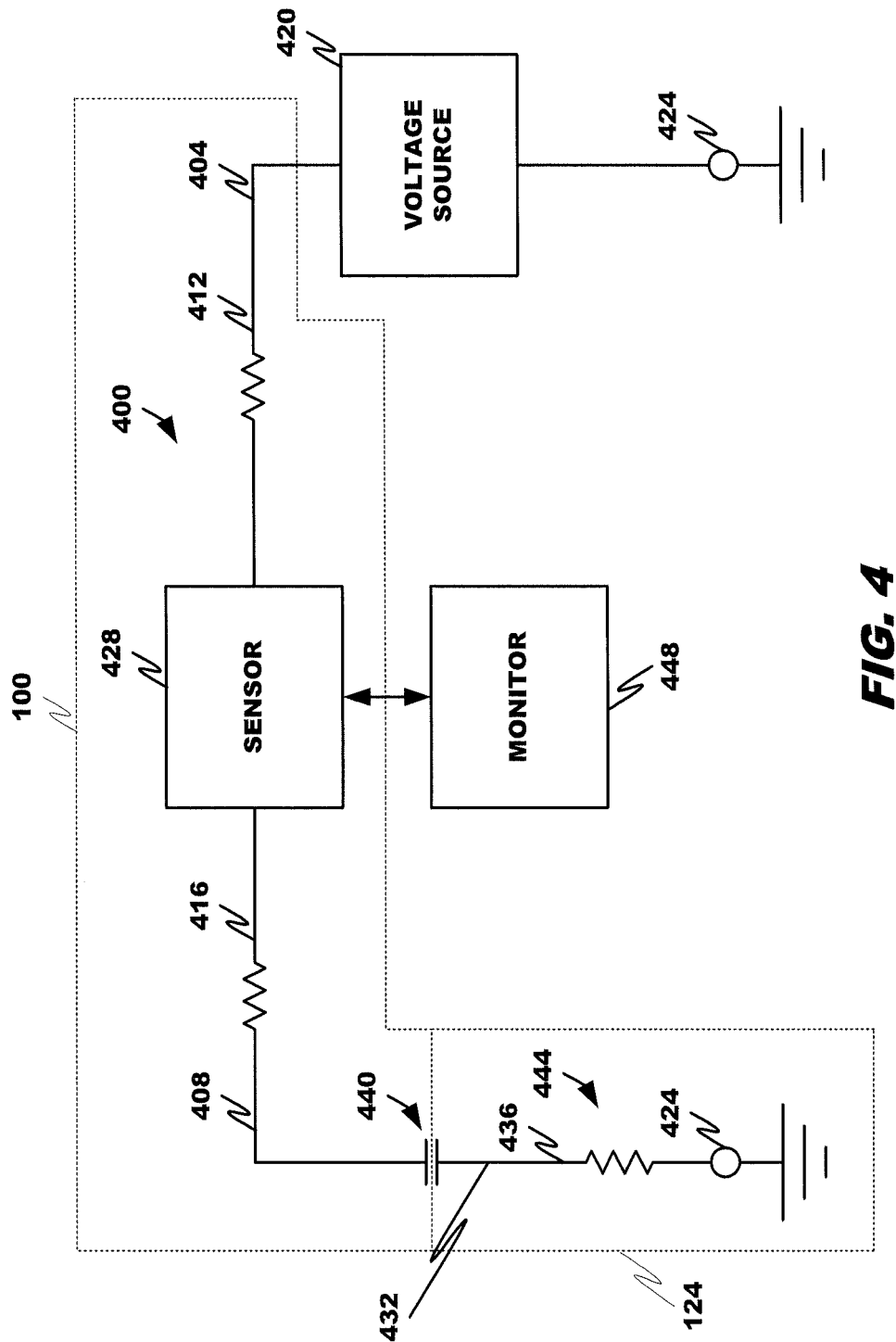
FIG. 4 is an electrical schematic according to an embodiment of the disclosure.

FIG. 4 depicts a third operational mode according to the disclosure. Unlike the first operational mode shown in FIG. 10, there is no direct electrical contact between the circuits 400 and 444 but a capacitance 440 exists between the circuits 400 and 444. The capacitance is too high for electrical current to pass into the circuit 444 when the insulation layer of the lead 124 is intact. However, when the insulation layer is damaged, such as by being cut, nicked, separated, or otherwise made discontinuous, the capacitance is lowered, thereby enabling electrical current to flow between the circuits. The sensor 428 is electrically connected to circuit 400 but may, alternatively, be electrically connected to the circuit 444.

Figure 5:
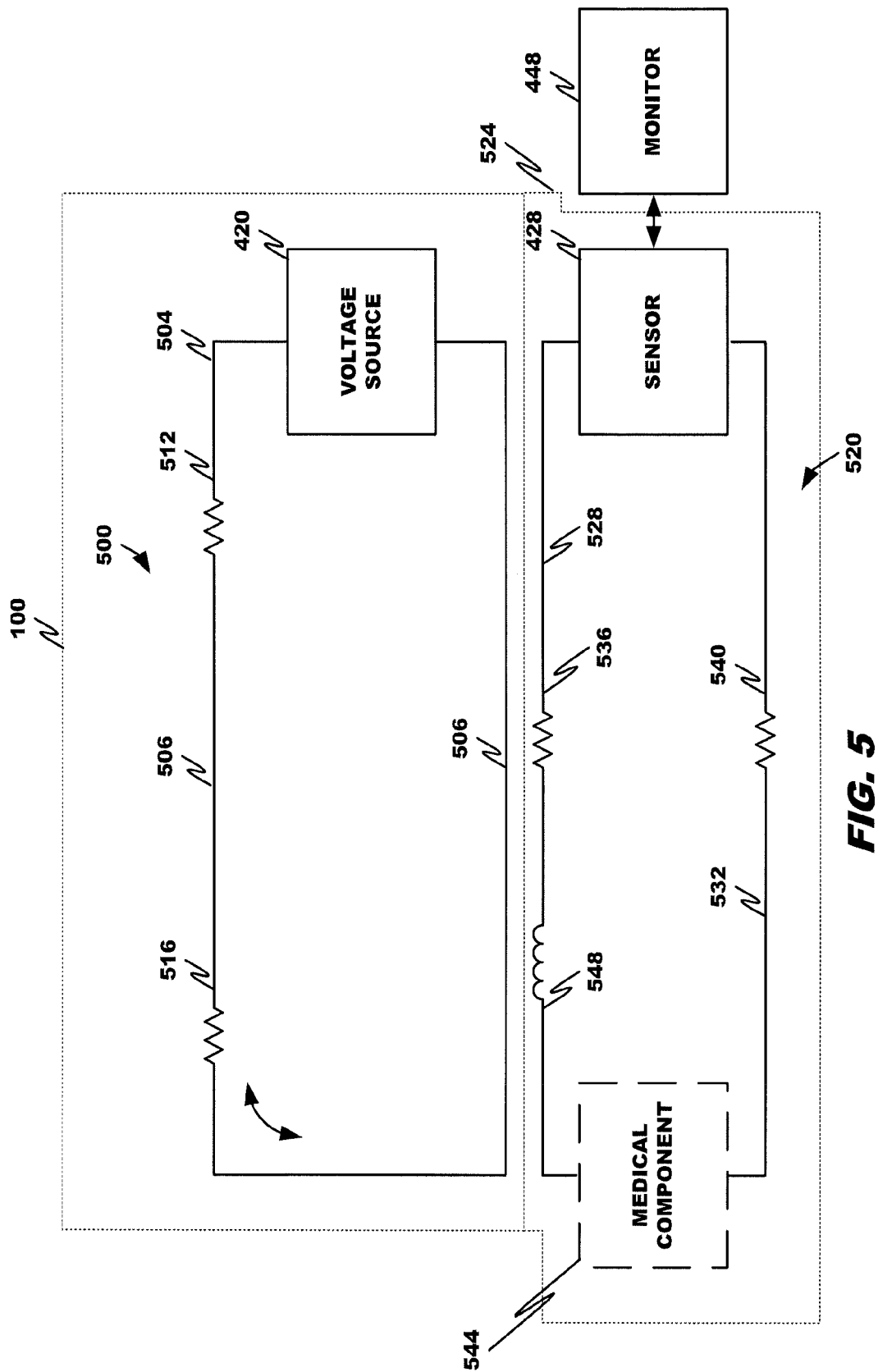
FIG. 5 is an electrical schematic according to an embodiment of the disclosure.

FIG. 5 depicts a fourth operational mode according to the disclosure. Unlike the second operational mode shown in FIG. 11, there is no direct electrical contact between the circuits 400 and 444 but, as shown by symbol 548, electrical current is induced in circuit 520 by electromagnetic or inductance coupling between the circuits 500 and 520. The degree of coupling and magnitude of the resulting current in the circuit 520 is a function of the integrity of the insulation layer on the lead 524. In other words, the magnitude of the electrical current induced by the flow of electricity in circuit 500 when the insulation layer is undamaged is different from that when the insulation layer is damaged, such as by being cut, nicked, separated, or otherwise made discontinuous.

This list of operational modes is not intended to be exhaustive but only illustrative. One of ordinary skill in the art will appreciate that other operational modes are possible based upon the teachings of this disclosure.

In any of the above operational modes, the sensor 428 detects current flow or other electrical parameter, and a controller 448 interfaces with the sensor 428 to sense abnormal output and provide appropriate alarm signaling and other output to the physician. The monitor 448 comprises a microprocessor (not shown) and a computer readable medium containing microprocessor readable and executable instructions controlling the interaction with the sensor 428.

Figure 6:
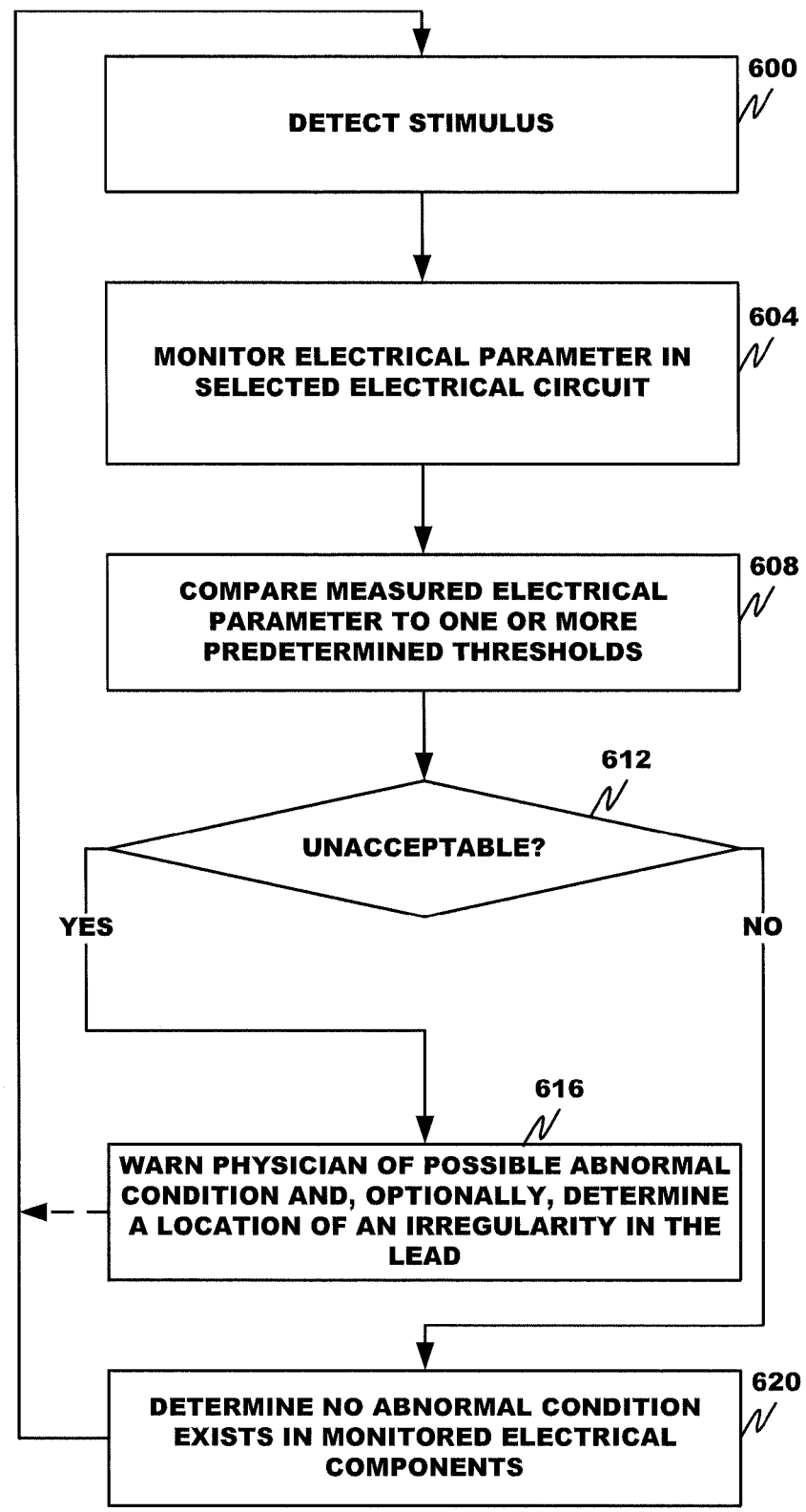
FIG. 6 is a flow schematic according to an embodiment of the disclosure.

FIG. 6 depicts a control logic according to an embodiment of the disclosure.

In step 600, the controller 448 detects a stimulus, such as input received from a physician.

In step 604, the controller 448 monitors input signaling from the sensor 428. The input signaling is related to the magnitude of one or more electrical parameters sensed by the sensor 428.

In step 608, the controller 448 compares the measured or sensed electrical parameters against one or more predetermined thresholds. The thresholds are commonly related to a state of integrity, health, or degree of damage of the insulating layer of the lead received by the sheath assembly.

In decision diamond 612, the controller 448, based on the comparison, determines whether the state of the insulating layer of the lead is acceptable or unacceptable. An unacceptable state is associated with a damaged or discontinuous insulating layer.

When the state is unacceptable, the controller 448, in step 616, warns the physician of a possible abnormal condition of the insulating layer and, optionally, determines a location in the body of the patient, of an irregularity in the lead's insulating layer. Alternatively, the physician may concurrently determine, from the marker, the approximate position of the irregularity. Optionally, the controller, after step 616, returns to step 600.

When the state is acceptable, the controller 448 returns to step 600.

A number of variations and modifications of the disclosure can be used. It would be possible to provide for some features of the disclosure without providing others.

For example, the measurement of lead state during lead removal can be used for lead removal techniques and devices other than sheaths, such as mechanical traction, mechanical devices, and energy devices.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device, comprising:
   a sheath comprising:
      an annulus to receive an implanted lead,
      a separator to substantially free the implanted lead from surrounding tissue, and
      an electrically conductive structure to interact electrically with a conductor of the lead, the electrically conductive structure comprising at least one conductive band around at least art of a circumference of the sheath, and the at least one conductive band comprising plural conductive bands positioned along a length of the sheath;
   a sensor to sense an electrical parameter associated with the lead to determine a condition of an insulation layer of the lead; and
   a controller operable to receive output from the sensor and determine when the condition of the insulation layer is not acceptable.

2. The device of claim 1, further comprising:
   a marker in spatial proximity to the electrically conductive structure to indicate a location of an unacceptable portion of the insulation layer.

3. The device of claim 1, wherein the electrically conductive structure is connected to a voltage source and the sensor.

4. The device of claim 1, wherein the conductor of the lead is connected to the sensor and wherein the electrically conductive structure is connected to a voltage source.

5. A device, comprising:
   a sheath comprising:
      an annulus to receive an implanted lead,
      a separator to substantially free the implanted lead from surrounding tissue, and
      an electrically conductive structure to interact electrically with a conductor of the lead;
   a sensor to sense an electrical parameter associated with the lead to determine a condition of an insulation layer of the lead; and
   a controller operable to receive output from the sensor and determine when the condition of the insulation layer is not acceptable;
   wherein the electrically conductive structure is connected to the sensor.

* * * * *